United States Patent [19]

Walsingham et al.

[11] 4,059,606

[45] Nov. 22, 1977

[54] ORGANOSILICON COMPOUNDS

[75] Inventors: Richard Warren Walsingham; Ronald Sangster Stuart, both of Manchester, England

[73] Assignee: Imperial Chemical Industries Limited, London, England

[21] Appl. No.: 713,503

[22] Filed: Aug. 11, 1976

[30] Foreign Application Priority Data

Aug. 29, 1975 United Kingdom ............... 35706/75

[51] Int. Cl.$^2$ ................................................ C07F 7/08
[52] U.S. Cl. ............................ 260/448.2 B; 252/351
[58] Field of Search .................................. 260/448.2 B

[56] References Cited

U.S. PATENT DOCUMENTS

| | | | |
|---|---|---|---|
| 3,272,762 | 9/1966 | Ibbotson et al. | 260/448.2 B X |
| 3,505,377 | 4/1970 | Morehouse | 260/448.2 B |
| 3,654,195 | 4/1972 | Raleigh | 260/448.2 B X |

*Primary Examiner*—Paul F. Shaver
*Attorney, Agent, or Firm*—Cushman, Darby & Cushman

[57] ABSTRACT

Silane or siloxane/polyether compositions obtained by reaction of a terminally unsaturated mono-epoxide with an alcohol, followed by hydrosilation.

9 Claims, No Drawings

ORGANOSILICON COMPOUNDS

This invention relates to new and useful organosilicon compounds and to a process for the production thereof.

Among the many known organosilicon compounds are those in which a polyether residue is attached to silicon via a bridging group which has a hydroxy, acyloxy, alkoxy or aryloxy group attached thereto, i.e. compounds containing the group

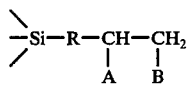

where R is an alkylene group or alkylene groups joined together via oxygen, A is a hydroxy, acyloxy, alkoxy or aryloxy group and B is a polyether residue. The case where A is a hydroxy group is the best known and most useful, the esterified and in particular the etherified derivatives being difficult to prepare in good yield and uncontaminated by unreacted hydroxylic material.

We have now discovered a new class of organosilicon compounds in which a polyether residue is attached to silicon via a bridging group which also carries an ether substituent which may be varied widely in nature in a manner which avoids the difficulties inherent in hitherto available products, including the presence of unreacted material and which provides a new method of modifying and controlling the solubility characteristics, hydrophilic/hydrophobic balance and surface activity of the products.

According to the present invention a new and useful class of organosilicon compounds comprises compounds having attached to silicon at least one group of the general formula

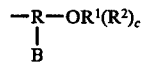     I where

     II or

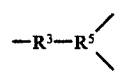     III $R^1$ is a group of valency $c + 1$ composed of C and H, C, H and F or, except when $R^3$ in formula II contains a single ether oxygen, of C, H and O in the form of ether linkages and having not more than 50 carbon atoms, not more than 12 of which are in aromatic rings, $R^2$ is a divalent group of formula $-CH(R^6)CH_2-$ (IV), $-CH=CH-$ (V) or $OR(B)-$ (VI) the remaining valency being bonded to a second silicon atom, $R^3$ is a divalent group composed of C, H and optionally O and having not more than 20 carbon atoms, $R^4$ is H or a monovalent hydrocarbon group having not more than 6 carbon atoms, $R^5$ is a cycloaliphatic group having 5 or 6 carbon atoms and having the groups B and $-OR^1(R^2)_c$ attached to adjacent carbon atoms, $R^6$ is H or an alkyl group having not more than 5 carbon atoms, B is a polyether residue and $c$ is 0 or 1.

The trivalent group R is derived from an aliphatic or cycloaliphatic mono epoxide having a terminal olefinic double bond, after reaction with $R^7(OH)_b$ wherein $b$ is 1 or 2 and $R^7$ is $R^1$ or when $b$ is 1 may be $R^1C(R^6)=CH_2$ or $R^1C\equiv CH$, and hydrosilation. Typical such groups include, for example,

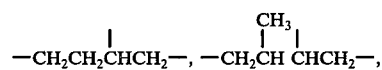

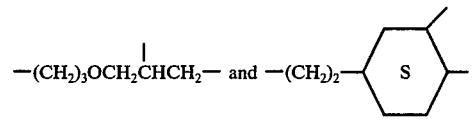

The group $R^1$ when monovalent may be an optionally fluorinated alkyl, aryl, alkaryl, aralkyl or cycloalkyl group or a non-terminally unsaturated alkenyl group such as, for example, a methyl, ethyl, propyl, butyl, decyl, octadecyl, phenyl, tolyl, nonylphenyl, benzyl, cyclohexyl or oleyl group, $H(CF_2)_4CH_2-$, $(CF_3)_2CH-$ or $C_6HF_4-$ or a group composed of C, H and O such as $CH_3OCH_2CH_2-$, $CH_3(OCH_2CH_2)_2-$, $C_2H_5(OCH_2CH_2)_3-$, $C_6H_{11}(OCH_2CH_2)_5-$ $[OCH_2CH(CH_3)]_5-$ or $C_9H_{19}.C_6H_4(OCH_2CH_2)_8-$, and when divalent may be an alkylene, arylene or mixed alkylene-arylene group such as, for example, a methylene, ethylene, propylene, butylene or octylene group, the group $-C_6H_4.CH_2.C_6H_4-$ or $-C_6H_4C(CH_3)_2C_6H_4-$, a group composed of C, H and O such as $-CH_2CH_2OCH_2CH_2-$, $-CH(CH_3)CH_2OCH_2CH(CH_3)-$, $-(C_2H_4O)_3C_2H_4-$, $-(C_3H_6O)_2C_3H_6-$ or $-C_6H_4OC_6H_4-$.

The silicon compounds of our invention include silanes and siloxanes. The silanes are of the general formula $R^8_eG_fSiX_{4-e-f}$ where $R^8$ is a monovalent hydrocarbon group having not more than 10 carbon atoms, G is a group of formula (I) or denotes a link to a divalent group $R^2$, X is a hydrolysable group selected from chlorine and bromine and alkoxy, alkoxyalkoxy or acyloxy groups having not more than 4 carbon atoms, $e$ is 0, 1, 2 or 3, $f$ is 1, 2 or 3 but is preferably 1 and $e + f$ is 1, 2 or 3. $R^8$ may be an alkyl, aryl, alkaryl, aralkyl or cycloalkyl group, such as for example, a methyl, ethyl, propyl, butyl, octyl, decyl, tolyl, benzyl or cyclohexyl group. In general methyl and phenyl groups are preferred and methyl groups are especially preferred.

The group X may be, for example, chlorine or bromine, or a methoxy, ethoxy, propoxy, butoxy, 2-methoxyethoxy, ethoxyethoxy, acetyl, propionyl or butyryl group. Normally methoxy, ethoxy and 2-methoxyethoxy groups are preferred.

The siloxanes of our invention consist of units

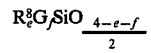

with or without units of the formula

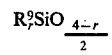

where $R^9$ is a monovalent hydrocarbon group having not more than 10 carbon atoms, optionally substituted by halogen or cyano, or a hydrogen atom provided that in no unit is there present both a substituted hydrocarbon group and a hydrogen atom bonded to silicon, and $r$ is 0, 1, 2 or 3. Suitable groups $R^9$ include, for example, hydrogen, methyl, ethyl, propyl, butyl, octyl, decyl, tolyl, benzyl, cyclohexyl, γ-chloropropyl, γ-chloroisobutyl, p-chlorophenyl, 3,3,3-trifluoropropyl, β-cyanoethyl and γ-cyanopropyl groups. In general methyl and phenyl groups are preferred and methyl groups are especially preferred.

The group B may be of the general formula $(OC_nH_{2n})_xOR^{10}$ where $R^{10}$ is hydrogen or an alkyl, aryl, alkaryl, aralkyl, cycloalkyl, acyl, carbamyl, alkoxycarbonyl or silyl group having up to 10 carbon atoms, $n$ is 2, 3 or 4, not all units necessarily being alike, and $x$ is an integer from 2 to 100. Suitable groups $R^{10}$ include, for example, methyl, ethyl, propyl, butyl, octyl, decyl, phenyl, tolyl, benzyl, cyclohexyl, acetyl, propionyl, phenyl-carbamyl, ethoxycarbonyl and trimethylsilyl groups. In general $R^{10}$ is preferably an alkyl group having not more than 5 carbon atoms, an acetyl or phenyl-carbamyl group.

The silicon compounds of our invention are produced by reacting a terminally unsaturated mono epoxide with a compound $R^7(OH)_b$, as hereinbefore defined, oxyalkylating the hydroxyether so produced with ethylene oxide and/or propylene oxide and/or tetrahydrofuran and reacting the product with a silicon compound containing at least one $\equiv$SiH group. When $R^7(OH)_b$ is a diol or a terminally unsaturated mono-ol, the resulting polyether will contain two unsaturated groups capable of hydrosilation and $c$ in the final product will have a value of 1, $R^2$ then forming a linking group to another silicon atom. The compound $R^7(OH)_b$ is reacted with the epoxide in known manner in the presence of a catalyst which may be acidic or basic, for example, a Lewis' acid such as boron trifluoride etherate or stannic chloride or a base such as sodium or potassium hydroxide. Potassium hydroxide is in fact particularly suitable. The oxyalkylation step is also carried out in presence of a catalyst which may in many cases be the same as that used for the previous reaction. When tetrahydrofuran is used, however, it is necessary that the catalyst be acidic, for example, such as boron trifluoride etherate. The hydroxyether may, if desired, be purified before the oxyalkylation.

In a preferred embodiment a partial sodium or potassium salt of $R^7(OH)_b$ is first prepared and purified to remove traces of moisture and alkali metal hydroxide which would give rise to polyglycol by-products during the oxyalkylation stage. This partial salt is then reacted with the unsaturated epoxide and the resulting hydroxyether partial salt heated under reduced pressure to remove unreacted $R^7(OH)_b$, if volatile, and other volatile impurities which could give rise to undesirable by-products at the oxyalkylation stage. Oxyalkylation with ethylene oxide and/or propylene oxide is then carried out at elevated temperature and pressure, e.g. 80°–120° C and 2–3 atmospheres pressure.

The oxyalkylated hydroxyether is neutralised and the terminal OH group on the polyether chain may be reacted in known manner to replace the hydrogen atom with another $R^{10}$ group as desired. Such reaction of the OH group may, if desired, be carried out after the hydrosilation stage or it may be desired to leave the OH group unreacted. This reaction of the OH group, if desired, may be effected by esterification with an acid anhydride or chloride, by etherification using any of the well known methods, e.g. by the Williamson ether synthesis or by use of a dialkyl sulphate, by urethane formation by reaction with an isocyanate, by carbonate formation by reaction with a chloroformate or carbonate or by silylation with a known silylating agent, for example, a chlorosilane or a silane having a labile —Si—N≡ bond.

The hydrosilation is carried out at elevated temperature either in absence or presence of a solvent which may be a hydrocarbon solvent or an ether solvent and in presence of a known catalyst for such hydrosilation reactions which may be a heterogeneous catalyst such as finely divided platinum metal, but is preferably a homogeneous catalyst in the form of a soluble compound or complex of a metal from Group VIII of the periodic table which is known to catalyse hydrosilation reactions. Such homogeneous catalysts include platinum compounds such as chloro-platinic acid, platinum alcoholates, platinum-olefine complexes and complexes with amines, phosphines and sulphides and platinum complexes containing silicon, rhodium or palladium complexes with, for example, triphenyl phosphine, and cobalt complexes such as dicobalt ostacarbonyl. Preferred catalysts are chloroplatinic acid and bis-diethyl-sulphide platinous chloride complex.

The silanes of our invention are prepared using as starting silicon compound a silane of general formula $R^8_eH_fSiX_{4-e-f}$ where $R^8$, X, $e$ and $f$ are as hereinbefore defined. $R^8$, when present, is preferably a methyl group. Particularly preferred reactants are $H.SiCl_3$, $H.Si(OMe)_3$, $H.Si(OEt)_3$, $H.Si(OCH_2CH_2OCH_3)_3$, $MeHSiCl_2$, $MeHSi(OMe)_2$, $MeHSi(OEt)_2$ and $MeHSi(OCH_2CH_2OCH_3)_2$.

The siloxanes of our invention may be prepared by hydrolysis or cohydrolysis and condensation of the silanes. They may also be prepared by the method described using as starting silicon compound a siloxane having at least one unit of general formula

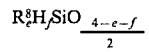

any remaining units being of formula

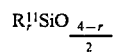

where $R^8$, $e$, $f$ and $r$ are as hereinbefore defined and $R^{11}$ is an optionally substituted monovalent hydrocarbon group as defined for $R^9$.

A preferred class of siloxane reactants has the general formula

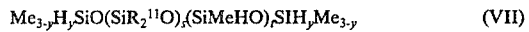 (VII)

where $y$ is 0 or 1, $s$ is 0 or a positive integer and $t$ is an integer of at least 1. It is particularly preferred that $R^{11}$ be a methyl group.

The introduction of a limited degree of branching into the starting siloxanes by inclusion of suitable branching units in amounts not exceeding 1 such unit for every 10 difunctional units also results in useful reactants. Suitable branching units are $R^{11}SiO_{3/2}$, $H.SiO_{3/2}$ and $SiO_2$.

In addition to their use in preparing the siloxanes of our invention the silanes may be used for a wide variety of other purposes including the surface treatment of finely divided solids such as pigments and fillers for plastics, rubbers, paints and inks to modify their surface properties and enhance their wettability and compatibility with a variety of liquid or resinous materials and to aid their dispersion in and reinforcement of plastics and elastomeric materials. The siloxanes are useful as nonionic surface active agents in a variety of applications including fibre treatment, emulsification, heat sensitisation of latices, cell structure control in expanded plastics and elastomers, and wetting of surfaces generally including low energy surfaces. They are particularly useful as a class because variation of R' gives additional control of HLB value, solubility characteristics and other physical properties not obtainable with previously known polysiloxane-polyoxyalkylene copolymers which depend mainly on siloxane to polyether ratio and oxyethylene content for property variation.

Our invention is further illustrated by the following examples in which all parts and percentages are by weight except where otherwise stated.

EXAMPLE 1

A solution containing 5.0 mole % sodium methoxide in methanol was prepared by adding 2.3 parts of sodium to 64.0 parts of methanol in a reaction flask protected by nitrogen. 114.0 Parts of allylglycidyl ether were added dropwise to the solution at between 60° and 80° C. The solution was maintained at 80° C for 1.0 hour on completing the addition after which material volatile up to 80° C at 20 mm Hg pressure was removed leaving a residue consisting of 4,8-dioxa-6-hydroxynon-1-ene, 10 mole % sodium salt.

146 Parts of the residue were reacted with 528 parts of ethylene oxide at 95° C and 40 psig by the well established procedure for oxyalkylation of alcohols and gave 674 parts of condensate. Basic material and volatiles were removed from the condensate by treating with synthetic magnesium silicate at 110° C and 20 mm Hg pressure followed by filtration. The so-produced polyether was a light amber oil with a hydroxyl value of 83 mg KOH g$^{-1}$ and an unsaturation value of 1.48 m.eq. g$^{-1}$.

337 parts of the so-prepared polyether were acetylated by heating at 140° C for 2.0 hours with 102 parts of acetic anhydride. Excess acetic anhydride was removed by heating at 140° C and 20 mm Hg pressure leaving a product that had no hydroxyl peak in its infrared spectrum.

78.8 parts (a 10% molar excess) of the acetylated polyether were reacted at 120° C for 4.0 hours with 100 parts of a polysiloxane of average formula

in 180 parts of toluene using 0.0228 part of bis(diethylsulphide) platinum (II) chloride as a catalyst to effect the hydrosilylation reaction. The polysiloxane was prepared from the appropriate chlorosilanes by a standard hydrolysis and equilibration process well established in the field of polysiloxane chemistry. The product was a light amber oil of viscosity 400 cP which had an infrared spectrum that showed only a trace of unreacted SiH was present. When applied at a 0.5% level to polyethylene terephthalate fibre, a significant reduction in fibre/fibre and fibre/steel friction was observed.

EXAMPLE 2

337 Parts of the unacetylated polyether of Example 1 in 350 parts of toluene were reacted with 66 parts of trimethylchlorosilane at 120° C for 3.0 hours. The devolatilised product gave an infrared spectrum which showed that only a trace of hydroxyl ended polyether remained in the sample.

82.1 parts of the so prepared trimethylsilyl end capped polyether were reacted with 100 parts of the polysiloxane used in Example 1 in the manner described in Example 1. The product was a light amber oil of viscosity 470 cP which contained only a trace of unreacted SiH. The product was an effective lubricant for polyethylene terephthalate fibre.

EXAMPLE 3

146 Parts of 4,8-dioxa-6-hydroxynon-1-ene, 10 mole % sodium salt were prepared as in Example 1. This material was reacted with 440 parts of ethylene oxide followed by reaction with 116 parts of propylene oxide at 95° C and 40 psig by the well established procedure for the oxyalkylation of alcohols and gave 702 parts of condensate which was neutralised and devolatilised in the manner described in Example 1. The product was a light brown amber oil with a hydroxyl value of 80 mg KOH g$^{-1}$ and an unsaturation value of 1.43 m.eq g$^{-1}$.

77.2 Parts of the so prepared hydroxyl ended polyether were reacted with 28.6 parts of a polysiloxane of average formula

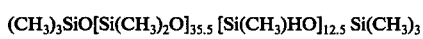

in 110 parts of toluene using 0.0228 part of bis(diethylsulphide) platinum (II) chloride as in Example 1. The polysiloxane was prepared as described in Example 1. The product was a light amber oil of viscosity 1400 cP which was readily soluble in water and which behaved as an efficient surfactant in the production of rigid polyurethane foam.

EXAMPLE 4

146 Parts of 4,8-dioxa-6-hydroxynon-1-ene, 10 mole % sodium salt were prepared in the manner described in Example 1. This material was reacted with 308 parts of ethylene oxide at 95° C and 40 psig by the well established procedure for the oxyalkylation of alcohols and gave 454 parts of condensate which was neutralised and devolatilised in the manner described in Example 1. The product was a light amber oil with a hydroxyl value of 123 mg KOH g$^{-1}$ and an unsaturation value of 2.20 m.eq g$^{-1}$.

49.9 parts of the so prepared polyether were reacted with 24.4 parts of 1,1,1,3,5,5,5-heptamethyltrisiloxane in 75 parts of toluene using 0.0228 part of bis(diethylsulphide) platinum (II) chloride as catalyst. The trisiloxane was prepared by the cohydrolysis of appropriate chlorosilanes followed by distillation. The product was a brown oil of viscosity 45 cP which was an efficient wetting/spreading agent for aqueous systems. A 1% solution of the product in water had a surface tension of 21 dynes cm$^{-1}$.

EXAMPLE 5

146 Parts of 4,8-dioxa-6-hydroxynon-1-ene, 10 mole % sodium salt were prepared in the manner described in Example 1. This material was reacted with a mixture of 780 parts of ethylene oxide and 780 parts of propylene oxide at 95° C and 40 psig under the conditions of Example 1 and gave 1706 parts of condensate which was neutralised and devolatilised as in Example 1. The product was a light amber oil with a hydroxyl value of 33 mg KOH g$^{-1}$ and an unsaturation value of 0.59 m.eq g$^{-1}$.

853 Parts of the so prepared polyether were acetylated by reacting with 102 parts of acetic anhydride under the conditions of Example 1. 192 Parts of the acetylated polyether were reacted with 73.0 parts of a polysiloxane of average formula

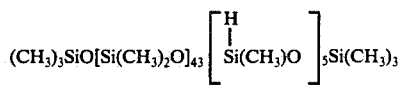

in 260 parts of toluene using 0.0228 part of bis(diethylsulphide) platinum (II) chloride as catalyst under the conditions of Example 1. The product was a light amber oil of viscosity 600 cP which was a useful surfactant in the production of flexible polyurethane foam.

EXAMPLE 6

192 Parts of the acetylated polyether used in Example 5 were reacted with 6.8 parts of a polysiloxane of average formula

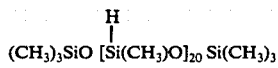

in 150 parts of toluene using 0.0228 parts of bis(diethylsulphide) platinum (II) chloride as catalyst under the conditions of Example 1. The product was a light amber oil of viscosity 1000 cP which was found to be a temperature sensitive coagulant for styrene butadiene latex.

EXAMPLE 7

4,8,11-Trioxa-6-hydroxydodec-1-ene was prepared by reaction of 150 parts of 2-methoxyethanol with 114.0 parts of allylglycidyl ether in the presence of 5.6 parts of potassium hydroxide and was purified by distillation under reduced pressure. 180 Parts of the product and 1.63 parts of potassium hydroxide were reacted with 567 parts of ethylene oxide under the conditions of Example 1 and the condensate purified as described in Example 1. The product polyether was a light amber oil with a hydroxyl value of 81 mg KOH g$^{-1}$ and an unsaturation value of 1.34 m.eq g$^{-1}$.

82.1 Parts of the so produced polyether were reacted with 100 parts of the polysiloxane used in Example 1 in 180 parts of toluene using 0.0228 part of bis(diethylsulphide) platinum (II) chloride as catalyst under the conditions of Example 1. The product was a light amber oil of viscosity 750 cP which was an effective lubricant for polyethylene terephthalate fibre.

EXAMPLE 8

6.5 parts of potassium hydroxide were dissolved in 150 parts of cyclohexanol in a reaction flask protected by nitrogen. The solution was heated to distil off 52.7 parts of a cyclohexanol/water mixture leaving 103.8 parts of a residue which consisted of 90 parts of cyclohexanol and 13.8 parts of potassium cyclohexoxide. 114 Parts of allylglycidylether were added to the residue at 80° C which was then reacted with a mixture of 780 parts of ethylene oxide and 780 parts of propylene oxide at 95° C and 40 psig under the conditions of Example 1 and gave 1778 parts of condensate which was devolatilised and neutralised as in Example 1. The so-prepared polyether was a light amber oil with a hydroxyl value of 31.5 mg KOH g$^{-1}$ and an unsaturation value of 0.565 m.eq. g$^{-1}$.

887 parts of the so-prepared polyether were acetylated by reacting with 102 parts of acetic anhydride under the conditions of Example 1. 200 Parts of the acetylated polyether were reacted with 73 parts of the polysiloxane of Example 5 in 270 parts of toluene using 0.0228 part of bis(diethylsulphide) platinum (II) chloride as catalyst under the conditions of Example 1. The product was a light amber oil of viscosity 700 cP which was a useful surfactant in the production of flexible polyurethane foam.

EXAMPLE 9

A 5 mole % alkoxide solution was prepared by adding 2.3 parts of sodium to 106 parts of diethyleneglycol in a flask protected by nitrogen. 228 Parts of allylglycidylether were added to the alkoxide solution under the conditions of Example 1 giving 336 parts of residue which was reacted with a mixture of 1560 parts of ethylene oxide and 1560 parts of propylene oxide at 95° C and 40 psig under the conditions of Example 1 and gave 3456 parts of a condensate which was devolatilised and neutralised as in Example 1. The so produced polyether diol was a light amber oil with a hydroxyl value of 32.4 mg KOH g$^{-1}$ and an unsaturation value of 0.58 m.eq. g$^{-1}$.

863.5 Parts of the so prepared polyether were acetylated by reacting with 102 parts of acetic anhydride under the conditions used in Example 1.

39.0 parts of the so prepared acetylated polyether were mixed with 192.0 parts of the acetylated polyether of Example 5 and the blend reacted with 8.15 parts of a polysiloxane of average formula

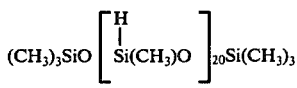

in 200 parts of toluene using 0.0274 part of bis(diethylsulphide) platinum (II) chloride as catalyst under the conditions of Example 1. The product was a light amber oil of viscosity 1000 cP which was found to be a temperature sensitive coagulant for styrene butadiene latex.

EXAMPLE 10

174.2 Parts of 4,8-dioxa-6-hydroxyundeca-1,10-diene (glycerol α,α-diallyl ether), 10% sodium salt were prepared by reaction of 81.2 parts of allyl alcohol with 114.0 parts of alkylglycidyl ether in the presence of 8.0 parts of sodium allyloxide and purified by distillation under reduced pressure.

87.1 parts of the residue prepared as described above were reacted with a mixture of 860 parts of ethylene oxide and 968 parts of propylene oxide at 95° C and 40 psig under the conditions of Example 1 and gave 1240 parts of condensate after neutralisation and devolatilisation as in Example 1. The product was a pale yellow oil with a hydroxyl value of 23 mg KOH g$^{-1}$ and an unsaturation value of 0.81 m.eq. g$^{-1}$.

650 Parts of the so prepared polyether were acetylated by reacting with 54 parts of acetic anhydride under the conditions of Example 1.

84 Parts of the acetylated polyether were reacted with 4.3 parts of the polysiloxane of Example 9 in 40 parts of toluene using 0.0274 parts of bis(diethylsulphide) platinum II chloride as catalyst under the conditions of Example 1.

The product was a light amber viscous oil which was useful as a temperature sensitive coagulant for styrene-butadiene latex.

We claim:

1. A polysiloxane of the formula:

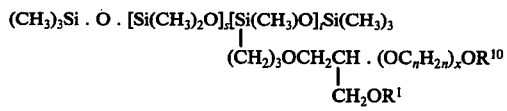

wherein
R$^1$ is lower alkyl, lower alkoxylower alkyl or cyclohexyl group,
R$^{10}$ is H, acetyl or trimethylsilyl,
n is 2, 3 or 4, all units C$_n$H$_{2n}$ not necessarily being alike,
x has a value from 2 to 100
s has a value from 0 to about 50 and
t has a value from 1 to about 20.

2. A polysiloxane as claimed in claim 1 having the formula:

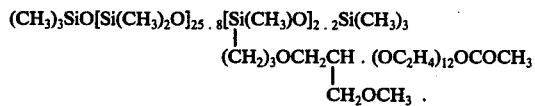

3. A polysiloxane as claimed in claim 1 having the formula:

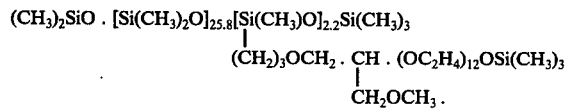

4. A polysiloxane as claimed in claim 1 having the formula:

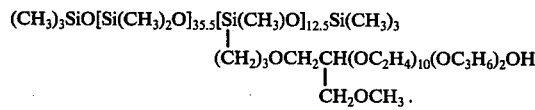

5. A polysiloxane as claimed in claim 1 having the formula:

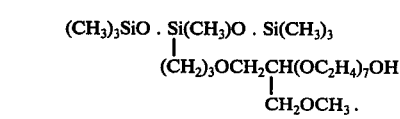

6. A polysiloxane as claimed in claim 1 having the formula:

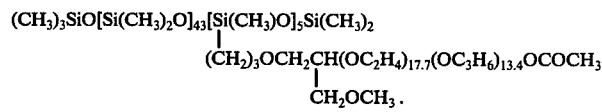

7. A polysiloxane as claimed in claim 1 having the formula:

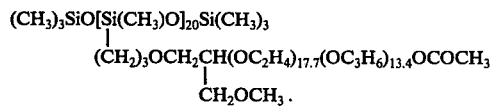

8. A polysiloxane as claimed in claim 1 having the formula:

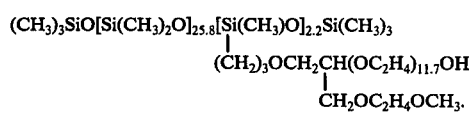

9. A polysiloxane as claimed in claim 1 having the formula:

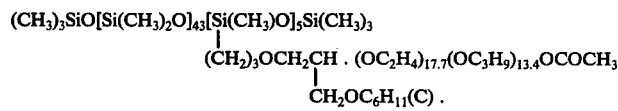

* * * * *